US00PP24926P3

(12) United States Plant Patent
Korlipara

(10) Patent No.: US PP24,926 P3
(45) Date of Patent: Sep. 23, 2014

(54) *ECHINACEA* PLANT NAMED 'ELEGANCE'

(50) Latin Name: ***Echinacea* hybrid**
Varietal Denomination: Elegance

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 169 days.

(21) Appl. No.: 13/573,974

(22) Filed: Oct. 16, 2012

(65) Prior Publication Data

US 2014/0109276 P1 Apr. 17, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

(56) References Cited

PUBLICATIONS

Upov Pluto Plant Variety Database 20140502, retrieved on May 22, 2014, retrieved from the Internet at <http://www.upov.int/pluto/en/index.jsp> for *Echinacea* 'Supreme Elegance' one page.*

* cited by examiner

*Primary Examiner* — June Hwu
(74) *Attorney, Agent, or Firm* — Klarquist Sparkman, LLP

(57) ABSTRACT

A new and distinct *Echinacea* plant named 'Elegance' characterized by enlarged disc florets forming an anemone-type inflorescence, dark pink ray florets and darker pink disc florets, inflorescences with dark centers when the disc florets are not fully opened, strong, dark stems that don't fall over with the weight of the large inflorescences, a medium short size and narrow, upright habit with excellent basal stem count, and excellent vigor.

1 Drawing Sheet

Botanical denomination: *Echinacea* hybrid.
Variety designation: 'Elegance'.

BACKGROUND OF THE INVENTION

The present invention relates to a new and distinct cultivar of *Echinacea* and given the cultivar name 'Elegance'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*×*Echinacea purpurea*.

Compared to *Echinacea* 'Pink Double Delight' (U.S. Plant Pat. No. 18,803), the new cultivar has larger, darker pink inflorescences and is shorter with a narrower and more compact habit, and strong stems that don't fall over.

Compared to *Echinacea* 'Cranberry Cupcake' (U.S. Plant patent application Ser. No. 12/931,237, now U.S. Plant Pat. No. 23,020), the new cultivar has larger inflorescences, darker green leaves, and a narrower habit.

This new *Echinacea* cultivar is distinguished by:

1. enlarged disc florets forming an anemone-type inflorescence,
2. dark pink ray florets and darker pink disc florets,
3. inflorescences with dark centers when the disc florets are not fully opened,
4. strong, dark stems that don't fall over with the weight of the large inflorescences,
5. a medium short size and narrow, upright habit with excellent basal stem count, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Elegance' growing in the trial bed in full sun in early July in Canby, Oreg. A black cloth was used as a background to show the habit.

DETAILED PLANT DESCRIPTION

The following is a detailed description of the new *Echinacea* cultivar based on observations of two-year-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5th edition.

Plant:

*Type*.—Herbaceous perennial.

*Hardiness*.—USDA Zones 4 to 9.

*Size*.—Grows to about 34 cm wide and 66 cm tall to top of inflorescences.

*Form*.—Basal clump, with about 21 stems from the base.

*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 1 to 3 inflorescences per stem.

*Size*.—To 58 cm tall to a terminal inflorescence and 1 cm wide at base.

*Internode length*.—1 cm to 7 cm.

*Surface texture*.—Strigose.

*Color*.—Yellow Green 146C strongly tinted Greyed Purple 187A.

Leaf (basal):

*Type*.—Simple.

*Shape*.—Ovate to lanceolate.

*Arrangement*.—Basal.

*Blade size*.—Grows to 8.5 cm long and 5 cm wide.

*Margins*.—Serrate.

*Apex*.—Acute.

*Base*.—Attenuate.

*Surface texture*.—Strigose on both sides.

*Venation*.—Pinnate, with 3 main veins from the base, Yellow Green 149D on top and bottom side.

*Color*.—Topside Green N137A, bottom side closest to Yellow Green 147B.

*Petiole description*.—Grows to 17 cm long and 3 mm wide above the clasp, sparsely strigose, Yellow Green 147C on sides, tinted Greyed Purple 187A toward the base.

Leaf (stem):

*Type*.—Simple.

*Shape*.—Lanceolate.

*Arrangement*.—Alternate.

*Blade size*.—Grows to 9.5 cm long and 4 cm wide.

*Margins*.—Slightly undulate.

*Apex*.—Acuminate.

*Base*.—Attenuate.

*Surface texture*.—Strigose on both sides.

*Venation*.—Pinnate, with 3 main veins from the base, Yellow Green 149D on top and bottom side.

*Color*.—Topside Green N137A, bottom side closest to Yellow Green 147B

*Petiole description*.—On all but upper leaves, clasping, grows to 4 cm long and 3 mm wide above the clasp, strigose, leaf sides Green N137A, top center Greyed Purple 183A, bottom side Yellow Green 147D.

Inflorescence:

*Type*.—Composite on terminal stalked heads.

*Number of flowering stems per plant*.—About 21.

*Flowering stem*.—Grows to 58 cm tall from the base of the plant to the terminal inflorescence and can grow to 22 cm long from the top stem leaf to the base of an inflorescence; branched with 1 to 3 inflorescences per stem; diameter growing to 9 mm wide near the inflorescence; strigose; Yellow Green 146C strongly tinted Greyed Purple 187A.

*Size*.—Grows to 10 cm wide and 6.5 cm deep as disc enlarges.

*Form*.—Ray florets held slightly reflexed, mature disc is conic.

*Immature inflorescence*.—Grows to 5.5 cm wide and 2 cm deep, ray florets held at a 10 degree angle from the horizontal and rolled up so only the back color shows, Purple N77B, disc color Greyed Purple N186A

*Ray florets*.—Without pistil or stamen, about 20 in number, grow to 47 mm long and 10 mm wide, oblanceolate with the tip two-toothed, tips acute, entire margins, base attenuate, glabrous on both sides; top and bottom side between Red Purple 64C and Purple N77B.

*Disc*.—Flat becoming conic, growing to 45 mm deep and 70 mm wide with maturity, Greyed Purple N186A when disc florets are closed to Red Purple 59C when disc florets are open.

*Disc florets*.—About 400 in number, each with 1 pistil and 4 sterile stamen, grow to 30 mm long and 6 mm wide, each with one persistent, very stiff linear bract (15 mm long with the Greyed Purple 187A at apex blending to Orange 26A then Yellow Green 145D blending to White 155A); corollas 14 mm to 25 mm long and 5 mm to 6 mm wide, tubular at base (2.5 mm to 3 mm long and 1.5 mm wide, 152C) then oblanceolate, margin entire, with acute tips variable (two toothed to three lobed), base attenuate, glabrous on both sides, topside Red Purple 64A, bottom side Purple N77A; pistil 10 mm long, ovary 5 mm long, White NN155A, style 4 mm long Red Purple 65D, 2-branched stigma spreading, Greyed Purple 187A; stamen 4 mm long, filaments 3 mm long, threadlike, Yellow Green 145D, anthers none, pollen none.

*Phyllaries*.—In 4 leafy series, area grows to 37 mm wide and 10 mm deep, lobes lanceolate in shape, reflexed, grow to 13 mm long and 3 mm wide, both sides strigose and Yellow Green 147B, margins strigose, tip acute.

*Receptacle*.—Grows to 14 mm wide and 13 mm deep, White NN155B.

*Bloom period*.—July through October in Canby, Oreg.

*Fragrance*.—Light, floral.

*Lastingness*.—Each inflorescence lasts about two weeks in Canby, Oreg.

*Seeds*.—None.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

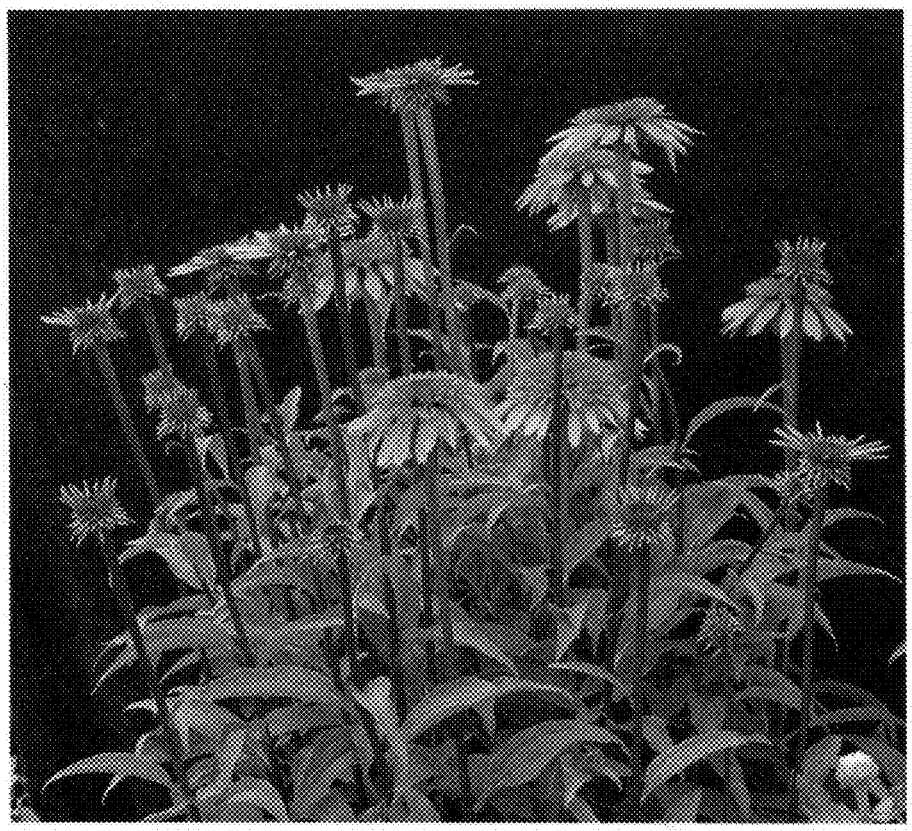

* * * * *